(12) United States Patent
Leipold et al.

(10) Patent No.: US 9,187,720 B2
(45) Date of Patent: Nov. 17, 2015

(54) SANITARY PRODUCT IN PIECE FORM

(75) Inventors: Joachim Leipold, Reutlingen (DE); Matthias Fritz, Gomaringen (DE); Edgar Jaeschke, Filderstadt (DE)

(73) Assignee: BUCK-CHEMIE GMBH, Herrenberg (DE)

( * ) Notice: Subject to any disclaimer, the term of this patent is extended or adjusted under 35 U.S.C. 154(b) by 0 days.

(21) Appl. No.: 14/115,892

(22) PCT Filed: Apr. 27, 2012

(86) PCT No.: PCT/EP2012/001818
§ 371 (c)(1),
(2), (4) Date: Jan. 16, 2014

(87) PCT Pub. No.: WO2012/152388
PCT Pub. Date: Nov. 15, 2012

(65) Prior Publication Data
US 2014/0349904 A1    Nov. 27, 2014

(30) Foreign Application Priority Data
May 6, 2011 (DE) .......................... 10 2011 100 859

(51) Int. Cl.
| | | |
|---|---|---|
| *C11D 1/02* | (2006.01) | |
| *C11D 3/32* | (2006.01) | |
| *C11D 3/50* | (2006.01) | |
| *C11D 17/00* | (2006.01) | |
| *A61L 9/012* | (2006.01) | |
| *A61L 9/04* | (2006.01) | |
| *A61L 9/05* | (2006.01) | |

(52) U.S. Cl.
CPC ............ *C11D 17/0026* (2013.01); *A61L 9/012* (2013.01); *A61L 9/048* (2013.01); *A61L 9/05* (2013.01)

(58) Field of Classification Search
CPC .......... C11D 1/02; C11D 3/32; C11D 3/3719; C11D 3/50; C11D 17/0056
USPC .............. 510/191, 192, 426, 475; 134/22.11, 134/22.14, 22.19, 39, 42
See application file for complete search history.

(56) References Cited

U.S. PATENT DOCUMENTS

| | | |
|---|---|---|
| 3,654,167 A | 4/1972 | Akrongold et al. |
| 4,666,671 A | 5/1987 | Purzycki et al. |
| 5,500,209 A | 3/1996 | Ross et al. |
| 6,111,055 A | 8/2000 | Berger et al. |
| 6,242,509 B1 | 6/2001 | Berger et al. |
| 6,423,324 B1 | 7/2002 | Murphy et al. |
| 8,444,771 B2 * | 5/2013 | Leipold et al. ............. 134/22.18 |
| 8,461,093 B2 | 6/2013 | Leipold et al. |
| 8,835,371 B2 | 9/2014 | Leipold et al. |
| 2004/0186263 A1 | 9/2004 | Pavlin |
| 2011/0002871 A1 * | 1/2011 | Leipold ........................ 424/76.1 |
| 2012/0251477 A1 * | 10/2012 | Pliszka ........................ 424/76.7 |
| 2013/0130962 A1 | 5/2013 | Leipold et al. |
| 2014/0037569 A1 | 2/2014 | Leipold et al. |
| 2014/0356311 A1 | 12/2014 | Leipold et al. |

FOREIGN PATENT DOCUMENTS

| | | | |
|---|---|---|---|
| DE | 197 10 635 A1 | 9/1998 | |
| DE | 10 2008 051173 A1 | 4/2010 | |
| EP | 0 057 839 A1 | 8/1982 | |
| EP | 0 864 637 A1 | 9/1998 | |
| EP | 1504769 A1 | 2/2005 | |
| EP | 1 553 162 A1 | 7/2005 | |
| EP | 1553162 * | 7/2005 | ............. C11D 17/00 |
| EP | 1 632 251 A1 | 3/2006 | |
| WO | 2004083280 A1 | 9/2004 | |
| WO | 2009100962 A1 | 8/2009 | |
| WO | 2014016098 A1 | 1/2014 | |

* cited by examiner

*Primary Examiner* — Brian P Mruk
(74) *Attorney, Agent, or Firm* — Kriegsman & Kriegsman

(57) ABSTRACT

The invention relates to the use of a sanitary product in piece form for use in the cistern of a toilet, which product comprises at least two different gel formers (1, 2) and fragrances, wherein one gel former (gel former 1) forms gels with hydrophobic liquids, which gels are insoluble or scarcely soluble in water, and the other gel former (gel former 2) is water-soluble or water-dispersible and wherein the product is transparent, gradually flushes away and releases fragrances, and gel formers 1 and 2 are in one phase.

15 Claims, No Drawings

SANITARY PRODUCT IN PIECE FORM

The present invention relates to a product in piece form for scenting toilets that is provided for use in a cistern.

Toilet cleaners which simultaneously serve as air fresheners by scenting the toilet area are known in the prior art. These are generally disposed in a holder or in a basket or cage-like container in the toilet bowl at a position through which incoming flush water passes during each flushing operation, as a result of which the product is gradually used up.

The life of these toilet cleaners is therefore determined by the number of flushes in the toilet in whose toilet bowls they are disposed. This attained life and the content of fragrances for scenting the room are regularly oriented to use by a family of three to four, meaning that adequate room scenting can no longer take place if the household or the place in whose area the toilet containing the cleaner is located is used by fewer people and/or not constantly. At the same time, the flush-away regulators present in such cleaning products, in the form e.g. of nonionic surfactants, ensure that the fragrances are more or less retained and cannot evaporate into the vicinity of the toilet area.

DE 197 10 635 A1 teaches a product which serves for attaching to the toilet rim and which achieves adequate and permanent room scenting even in the event of a small number of flush cycles. The product comprises fragrances and is in the form of a lyogel, i.e. a liquid-rich disperse system of at least two components, namely a solid, colloidally dispersed gel former and a liquid as dispersant. These products dissolve as they are flushed over by water in a basket in general after 100 to 250 flushes and also conform to consumer wishes as a result of their transparency.

U.S. Pat. No. 4,666,671 discloses air freshening blocks for the toilet area which comprise gel formers, fragrances and solvents. Even though these gel air freshening blocks can achieve constant room scenting even in the case of toilets which are little used or not constantly used, these blocks serve exclusively for air freshening the toilet area and do not dissolve.

EP 1 553 162 B1 discloses products having a solid phase and a transparent gel phase based on polyamide resin with fragrances for scenting which serve for use in a WC cage. However, a disadvantage of these products is that the gel phase in the toilet cage does not dissolve as it is flushed over by water, but has to be disposed of as a residue.

EP 1 632 251 A1 discloses a scenting product for the sanitary sector which consists of two separate solid carriers. One of the carriers is transparent; the products are preferably two-colored in order to obtain an esthetically pleasing product.

Cleaning and/or scenting products which comprise surfactants, fragrances, sometimes also dyes, bleaches etc. and are extruded are known for use in cisterns. These products serve for storage in cold water, dissolve completely generally only after 400 or more flushes and are not transparent.

Furthermore, two-phase products for cisterns are known, for example the "Blink blue rinse" from Budich International, Hiddenhausen, which, besides a cleaning blue rinse, comprises a limescale-dissolving core as the second phase, or the "Bloo Power Core" form Jeyes which, besides a blue-flushing cleaning product shaped-body phase, comprises, as a second phase, a rapidly dissolving part with further active phases containing scent and foam.

The scenting of the toilet with the known cistern products, however, is slight since the known products are generally extruded cleaning product shaped bodies which can absorb only small amounts of fragrance since they would otherwise become sticky and unextrudable. Moreover, the in-tank products known hitherto do not satisfy consumer requirements with regard to transparency.

For use in a cistern, no product is hitherto known which can absorb high perfume concentrations, achieves long service lives in the water of the cistern, but nevertheless dissolves and is transparent.

The object of the present invention consists in indicating a sanitary product for the cisterns of toilets which fragrances the toilet area over a prolonged period, which dissolves gradually and is transparent.

This object is achieved by a product which comprises fragrances and at least two gel formers, where a first gel former (gel former 1) forms gels that are sparingly soluble or insoluble in water with hydrophobic liquids, and the second gel former (gel former 2) is water-soluble or water-dispersible, and gel formers 1 and 2 are in one phase.

According to the invention, a combination of at least two gel formers (gel formers 1 and gel formers 2) is used in the product.

One gel former (gel formers 1) serves for gel formation with the hydrophobic fragrances and is selected from the group of polyamide resins or olefin homopolymers and copolymers of two and more olefins.

The gel former from the group of polyamide resins that is used is preferably an ester-terminated polyamide (ETPA), an ester-terminated, dimeric-acid-based polyamide resin (ETDABP), an amide-terminated polyamide (ATPA) or a polyalkyleneoxy-polyamide (PAOPA). These polyamide resins can form transparent clear gels which are sparingly soluble or insoluble in water with hydrophobic liquids such as perfume oils and fragrances.

As gel formers 1 which is sparingly soluble or insoluble in water from the class of ester-terminated polyamides (ETPA), it is possible to use a composition of the formula

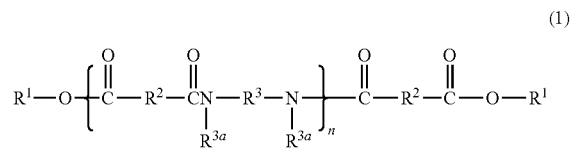

(1)

where n is a number of repeat units such that ester groups constitute from 10% to 50% of the total number of ester and amide groups; $R^1$, each time it appears, is independently selected from an alkyl or alkenyl group which contains at least 4 carbon atoms; $R^2$, each time it appears, is selected independently from a $C_{4-42}$-hydrocarbon group with the proviso that at least 50% of the $R^2$ groups have 30-42 carbon atoms; $R^3$, each time it appears, is selected independently from an organic group which contains at least 2 carbon atoms in addition to hydrogen atoms and optionally contains one or more oxygen and nitrogen atoms; and $R^{3a}$, each time it appears, is selected independently from hydrogen, $C_{1-10}$-alkyl and a direct bond to $R^3$ or a further $R^{3a}$, such that the N atom to which $R^3$ and $R^{3a}$ are both bonded is part of a heterocyclic structure which is defined in part by $R^{3a}$—N—$R^3$ such that at least 50% of the $R^{3a}$ groups are hydrogen.

Such compounds are described in EP 0 939 782 B1 of Arizona Chemical Co.

The ester-terminated, dimeric-acid-based polyamide resin (ETDABP) selected may be a compound of the following formula (2):

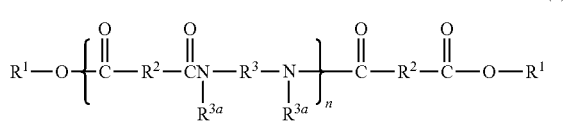

(2)

where n is a number of repeat units such that ester groups constitute from 10% to 50% of the totality of ester and amide groups; $R^1$, each time it appears, is selected independently from hydrocarbon groups; $R^2$, each time it appears, is selected independently from a $C_{2-42}$-hydrocarbon group, with the proviso that at least 10% of the $R^2$ group have 30-42 carbon atoms; $R^3$, each time it appears, is selected independently from an organic group which contains at least 2 carbon atoms in addition to hydrogen atoms, and optionally comprising one or more oxygen and nitrogen atoms; and $R^{3a}$, each time it appears, is selected independently from hydrogen, $C_{1-10}$-alkyl and a direct bond to $R^3$ or a further $R^{3a}$, such that the N atom to which $R^3$ and $R^{3a}$ are both bonded is part of a heterocyclic structure which is partially defined by $R^{3a}$—N—$R^3$.

Such compounds are described in EP 1 027 032 B1 of Arizona Chemical Co.

Furthermore, it is also possible to use olefin homopolymers and copolymers of two and more olefins as gel former 1. These compounds include e.g. the polybutadiene rubbers, the styrene-butadiene block polymers and copolymers, and also the polyisopropenes. It is also possible to use "random (block) polymers", which are prepared by 1,3-addition of butadiene or isoprene onto styrene or alpha-methyl styrene, the homopolymers or copolymers of ethylene and propylene, such as ethylene-propylene diene terpolymers, natural rubber and norbornene polymers, such as polydicyclopentadiene. The compounds from the group of olefin homopolymers and copolymers can also be partially hydrogenated.

Gel formers 1 from the group of polystyrene derivatives are preferably crosslinked polystyrene derivatives that are soluble in mineral oil, in particular alkylene styrene copolymers, such as, for example, the hydrogenated butylene/ethylene/styrene copolymers and the hydrogenated ethylene/propylene/styrene copolymers, which are obtainable for example in dissolved form from Penreco under the trade name Versagel M750 or Versagel M1600. These polymers themselves are obtainable from Shell as Kraton grades.

Within the context of the present invention, the gels gelled with gel formers 1 and the fragrances are sparingly soluble or insoluble or incompletely dispersible with water if ca. 0.5 gram of the product is left to stand for at least 24 hours with the addition of ca. 30 ml of tap water at room temperature and then afterwards, after shaking the vessel, the supernatant liquid is removed by decantation, this procedure being repeated at least 5 times over the course of 8 days, without complete dissolution/complete dispersion of the product being observed. If, moreover, after 43 days the product has dissolved to at least 10%, it can be used as a product within the meaning of the invention. In other words, those systems which have already completely dissolved after a few shake tests are unsuitable, and those products which pass into solution gradually after a prolonged shake cycle are suitable. In working example V3 described below in table 1, this is the case for the cistern of a real toilet after ca. 450 flushes for a start weight of 13.4 g.

The second gel former (gel formers 2) is water-soluble or water-dispersible. The desired solubility in water of the product and the desired flush numbers can be adjusted through this.

The second gel former is selected from the class of surfactants, water-soluble or water-dispersible polyamide resins or gel-forming natural or synthetic polymers.

The surfactants used are preferably gel-forming anionic or nonionic surfactants, with products containing surfactants as gel formers 2 being characterized by an additional cleaning effect.

It is essential that these surfactants are likewise gel formers since the products would otherwise become cloudy and lose the desired transparency.

The anionic surfactants require at least one water-solubilizing anionic group such as e.g. a carboxylate group, phosphate group, sulfate group, phosphonate group, sulfonate group and at least one lipophilic alkyl and/or aryl group having 8 to 30 carbon atoms. Additionally, further groups such as, for example, glycol or polyglycol ether groups, ester, ether and amide groups, hydroxyl groups, in each case in the form of the sodium, potassium, calcium, magnesium, zinc and ammonium and also the mono-, di- and trialkanol ammonium salts having 2 to 4 carbon atoms in the alkanol group may be present in the molecule.

In particular, the following compounds can be used as gel-forming anionic surfactants:

Acyl isethionates having 8 to 30 carbon atoms in the acyl group, acyl sarcosides having 8 to 30 carbon atoms in the acyl group, acyl taurides having 8 to 30 carbon atoms in the acyl group, alkanesulfonates (linear) having 8 to 30 carbon atoms, alkyl, aryl and/or alkenyl ether phosphates with an aliphatic hydrocarbon radical having 8 to 30 carbon atoms, alkyl polyglycol ether sulfates with preferably linear alkyl groups, having 8 to 30 carbon atoms, alkyl sulfates, alpha-sulfo fatty acid methyl esters of fatty acids having 8 to 30 carbon atoms, amid(o)ether carboxylic acids, protein fatty acid condensates (Lamepon® grades, Amisoft® grades), ether carboxylic acids with a linear alkyl group having 8 to 30 carbon atoms, fatty acid alkylene glycol esters, hydroxy sulfonates, linear alpha-olefin sulfonates having 8 to 30 carbon atoms, monoglyceride (ether) sulfates, sulfated hydroxyalkyl/aryl polyethylene and/or hydroxy alkylene-arylenepropylene glycol ethers, sulfosuccinic acid monoalkyl/-arylpolyoxyethyl esters having 8 to 30 carbon atoms in the alkyl/aryl group and 1 to 6 oxyethyl(propyl) groups, sulfosuccinic acid mono- and dialkyl/aryl esters having 8 to 30 carbon atoms in the alkyl/aryl group and sulfonates of unsaturated fatty acids having 8 to 30 carbon atoms and 1 to 6 double bonds.

Lauryl ether sulfates, fatty alcohol polyethylene glycol ether sulfate, laurylbenzenesulfonates, alkylpolyglycol ether phosphates can also be used.

Using the acidic alkylpolyglycol ether phosphates enables the pH of the product to be adjusted, so that an acidic product is also obtainable and the product can thus also be used as a limescale remover.

These acidic anionic surfactants are less sensitive than phosphoric acid esters to hardness formers in water such as calcium or magnesium ions, have a good lime-soap dispersibility, are very resistant to alkalis and are compatible with anionic, amphoteric and nonionic surfactants. Furthermore, they are corrosion-protecting, entirely biodegradable and conform to regulation (EC) No. 648/2004 on detergents.

The acidic alkyl polyglycol ether phosphates are obtainable for example under the trade name Phosfetal from Zschimmer & Schwarz, Lahnstein, Germany, Crafol from Cognis or Naxonac from Nease Performance Chemicals.

By using alkylbenzenesulfonates as a second gel former, an additional cleaning effect and moreover also a foam formation can likewise be achieved.

In a particularly preferred variant, both alkylbenzenesulfonate and fatty alcohol polyethylene glycol ether sulfate are used in the product as the second or further gel former.

As gel formers, it is also possible to use natural or synthetic polymers such as celluloses, in particular sodium carboxymethyl celluloses, hydroxyethyl celluloses, hydroxypropyl cellulose or else polysaccharides such as agar agar, gum arabic, carob seed flower or starch, polyacrylates, polysaccharides, polyvinyl alcohols or polyvinylpyrrolidone, alginates, diurethanes, gelatins or pectins.

Water-soluble or water-dispersing polyamide resins (gel former 2) that can be used are for example block copolymers of the formula hydrocarbon-polyether-polyamide-polyether-hydrocarbon, with preference being given to copolymers in which the polyamide block has the formula

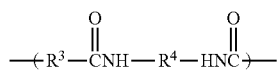

in which $R^3$ is a hydrocarbon and $R^4$ is selected from hydrocarbons and polyethers. Such compounds are described in EP 1 358 248 B1 from Arizona Chemical Co.

Furthermore, water-soluble polyamide resins that can be used are for example polyamide-6 or polyamide-4, which form gels with medium-polar or strongly polar liquids and are available from Arizona Chemical under the name Silvaclear PE400V or Silvaclear WF1500V. The water-soluble polyamide resin that is available from Arizona Chemical under the product number X54-188-152 can likewise be used.

The sole use of the second gel former (without first gel former) would lead, upon storing the product in water, to the product dissolving immediately or after a few flushes.

In this respect, the invention envisages the combination of the two gel formers together with perfume.

Fragrances which can be used are preferably mixtures of generally hydrophobic perfume oils.

The fragrance fraction in products with polyamide resins can be up to 70% by weight, meaning that a long-lasting scenting of the toilet is achieved via the product located in water in the cistern.

The concentration of the gel former (1) should be between 5 and 80% by weight, preferably between 8 and 60% by weight and particularly preferably between 15 and 50% by weight, that of the gel former (2) should be between 5 and 80% by weight, preferably between 8 and 60% by weight and particularly preferably between 15 and 50% by weight, and the concentration of the perfume should be in particular between 1 and 40% by weight, preferably between 3 and 30% by weight and particularly preferably between 4 and 15% by weight.

The concentration ratio between gel formers 1:gel former 2 should be between 95 and 5, preferably between 90 and 10 and particularly preferably between 80 and 20.

In order to achieve the desired fragrancing and the desired dissolution behavior, the two gel formers 1 and 2 should be present in the product in one phase.

The product according to the invention has on the one hand flush numbers of at least 150 in the case of steric hindrance such as, for example, at least partial covering with another material, and of more than 200 in the case of permanent storage in cold water, but on the other hand dissolves gradually so that no undesired residues remain in the cistern. In any case, the product with a mass of 50 g should have dissolved after preferably up to 500 and at most 800 flushes.

Moreover, we have been successful in providing such a product with high flush numbers for the cistern also as a product which can fragrance the toilet over a long period, and at the same time retaining the desired transparency of the product.

Within the context of the present invention, a product is transparent if it is transparent at the point of first use. Whether the product gradually loses its transparency in the course of use in the cistern is unimportant since at this point the product is no longer visible to the consumer.

The transparency of the product is determined by whether writing with decreasing size can be read through different layer thicknesses of the product. To ascertain the transparency of the product, the batches were poured into aluminum molds (internal dimension: 5 cm or 2.5 cm thickness×2 cm width× ca. 8 cm height), cooled overnight and pressed from the mold on the following day.

The legibility of lettering 3, 5 or 7 pixels in height, which was generated on an HP Laserjet 2100, was assessed, with a product being transparent within the context of the invention if at least one 7 pixel layer is legible through a 25 mm layer thickness; particularly good transparency is present if the legibility of a 5 or 3 pixel layer is still legible through a 49 mm-thick block.

The products according to the invention are further also characterized by an adequate hardness at room temperature. The products are cut-resistant and dimensionally stable at room temperature.

The invention also relates to a method for scenting toilets. The scenting takes place by placing the above-described sanitary product into the cistern of a toilet. The product dissolves gradually in cold water and continuously releases fragrances which scent the toilet.

The invention is described in more detail below by reference to working examples.

1. Working Examples According to the Invention:

The table below contains the different working examples according to the invention.

TABLE 1

| Material | E1 [%] initial weight | E2 [%] initial weight | E3 [%] initial weight | Manufacturer | |
|---|---|---|---|---|---|
| PE 400 V | 60 | 58 | | Arizona Chemical | Gel former 1 |
| AF 1900 | 2 | 7 | | Arizona Chemical | Gel former 1 |
| PA 1200 | | | 66 | Arizona Chemical | Gel former 1 |
| Phosfetal 201 | 23 | | | Zschimmer & Schwarz | Gel former 2 |
| Marlinat 242/90T | | 20 | 30 | Sasol | Gel former 2 |
| Orange Fun | 15 | 15 | 4 | Givaudan | Perfume |
| Initial weight of block | 31 g | 30.6 g | 13.4 g | | |
| Transparency through a 25 mm-thick block; lettering size 7 pixels | legible | legible | n.d. | | |
| Transparency | legible | no longer | n.d. | | |

TABLE 1-continued

| Material | E1 [%] initial weight | E2 [%] initial weight | E3 [%] initial weight | Manufacturer |
|---|---|---|---|---|
| through 49 mm-wide block; 3 pt lettering size | | legible | | |
| Transparency in cisterns after 12 h | becomes white | becomes white | remains transparent | |
| Surface tension | 54.4; 48.2; 45.9 | 56.7; 50.1; 47.6 | n.d. | |
| Foam | 80; 75; 50 | 90; 80; 75 | n.d. | |
| pH; 20.6° C. | 3.78 | 4.79 | n.d. | |
| Flush number | ca. 30 | ca. 30 | >450 | |

The alkyl polyglycol ether phosphate used was Phosfetal 205, obtainable from Zschimmer & Schwarz. The pH of a 1% solution is 2. The alkyl group is a C14-C18 group, the "polyglycol ether" group has between 1 and 3 glycol units.

Marlinat 242/90T consists of C12-C14-alcohol polyethylene glycol and propylene ether-(2 EO) sulfate, glycol triisopropanol ammonium salt (Sasol).

Determination of the Flush Numbers:

The flush numbers were determined by throwing the product into the cistern or suspending it in the cage, the fill level being ca. 8 liters of water at a temperature of 16° C.

Per flush, it was emptied completely and then refilled to 8 liters.

The number of flushes which were required to completely dissolve the product was then ascertained.

Experimental Evaluation:
1) Transparent, sometimes highly transparent masses are formed.
2) The masses are all surfactant- and perfume-containing.
3) Systems rendered acidic can be produced.
4) There are systems (e.g. E3) which have high flush numbers, similarly to extruded blocks, and remain transparent!

2. Comparative Experiments from the Prior Art:

TABLE 2

| | DE 197 10 635 | WO 99/66017 |
|---|---|---|
| Gel former | 31.6% polyoxyethylene 10 | 13% alkyl polyglycol ether 35 EO |
| Gel former | 19.2% polyoxyethylene 11 | 13% alkyl polyglycol ether 30 EO |
| Gel former | 5.3% Na stearate | |
| Fragrance | 32.60% | 6.50% |
| Other | 4.7% water 4.7% propylene glycol 0.09% dye 1.8% DBS, Na salt | 6% Marlinat 242/90T 0.003% dye 48% water 1.3% polyethylene glycol 6000 12% glycerol (86.5 percent strength) |
| Transparency | Not legible through 5th lettering at 49 mm layer thickness (becomes cloudy over time) | Very good, remaining |
| Solubility in water within fewer than 15 flush cycles in the cistern | Complete | Complete |
| Fragrance absorption | Up to 35% | ~6.5% |
| State of aggregation | solid, not dimensionally stable | High viscosity |
| pH (1% water dist.) | ca. 7 | ca. 7 |
| Foam number 1% solution | +60 mL | +80 mL |
| Surface tension 100 ms (1% solution) | 47 mN/m | 66 mN/m |
| Gel former | Stearate/nonionic surfactants | Nonionic surfactants |

Evaluation:

Although the systems to date have been able to be loaded with high concentrations of fragrance and are also transparent, they are neither solid enough, nor sufficiently flush-resistant to be used as products in the cistern. Moreover, they cannot be rendered acidic.

3. Table of Various Formulations According to the Invention

Table 3 gives various mixtures of gel formers 1 and 2 with the addition of perfume; the dissolution behavior is shown in tables 4 and 5.

TABLE 3

| | | Experiment name | | | | | | | | | | |
|---|---|---|---|---|---|---|---|---|---|---|---|---|
| | | AF TS 10 | AF TS 40 | A200 TS 10 | A200 TS 40 | PA TS 10 | PA TS 40 | Imb 5 | Imb 40 | Tego 5 | Tego 40 | Gelatin 40 |
| Raw material | Initial weight [%] | | | | | | | | | | | |
| Polyamide AF 1900 | | 87.2 | 67.0 | | | | | 90.7 | 68.5 | 82.9 | 68.7 | 68.9 |
| Polyamide A 200 | | | | 85.4 | 66.8 | | | | | | | |
| Polyamide PA 1200 | | | | | | 86.4 | 66.3 | | | | | |
| Marlinat 242/90T | | 8.9 | 28.0 | 10.3 | 28.6 | 9.3 | 29.3 | | | | | |
| Imbentin AG | | | | | | | | 4.7 | 27.8 | | | |
| Tego Carbomer 134 | | | | | | | | | | 13.1 | 27.8 | |
| Gelatin | | | | | | | | | | | | 27.5 |
| Perfume | | 3.9 | 5.0 | 4.3 | 4.6 | 4.3 | 4.4 | 4.6 | 3.7 | 4 | 3.5 | 3.6 |

TABLE 3-continued

| | Experiment name | | | | | | | | | | |
|---|---|---|---|---|---|---|---|---|---|---|---|
| | AF TS 10 | AF TS 40 | A200 TS 10 | A200 TS 40 | PA TS 10 | PA TS 40 | Imb 5 | Imb 40 | Tego 5 | Tego 40 | Gelatin 40 |
| Orange Fun PA/Perfume | 4.47% | 7.46% | 5.04% | 6.89% | 4.98% | 6.64% | 5.07% | 5.40% | 4.83% | 5.09% | 5.22% |
| G2/G1 | 10.21 | 41.79 | 12.06 | 42.81 | 10.76 | 44.19 | 5.18 | 40.58 | 15.80 | 40.47 | 39.91 |
| | 100.00 | 100.00 | 100.00 | 100.00 | 100.00 | 100.00 | 100.00 | 100.00 | 100.00 | 100.00 | 100.00 |

Imbentin AG: Imbentin AG/168/110 Kolb Chemie
Gelatin: Merck
Tego Carbomer: Goldschmidt AG
G2, G1: Gel former 2 and gel formers 1

4. Solubility Behavior of the Experiment According to the Invention from Table 3

The semiquantitative shaking and dissolving experiments with various gel formers 1/gel formers 2 combinations are shown in table 4 below.

TABLE 4

| | | 0 h | 24 h | 48 h | 72 h | 6 days | 8 days | 43 days | Initial weight ca. | Final weight | Difference | Dissolved fraction |
|---|---|---|---|---|---|---|---|---|---|---|---|---|
| Polyamide + Perfume | 95% AF 5% Orange Fun | transp. floats | insoluble, transp. | insoluble, transp. | insoluble, transp. | insoluble, transp. | insoluble | insoluble | 0.500 g | 0.48 g | 0.020 | 4.00% |
| | 77% AF 23% Orange Fun | transp. floats | insoluble, transp. | insoluble, transp. | insoluble, transp. | insoluble, transp. | insoluble | sparingly soluble | 0.500 g | 0.44 g | 0.060 | 12.00% |
| | 95% A 200 5% Orange Fun | transp. floats | insoluble, transp. | insoluble, transp. | insoluble, transp. | insoluble, cloudy | insoluble | insoluble | 0.500 g | 0.48 g | 0.020 | 4.00% |
| | 77% A 200 23% Orange Fun | slightly opaque, floats | insoluble, cloudy | insoluble, cloudy | insoluble, splits slightly | insoluble, cloudy | insoluble | sparingly soluble | 0.500 g | 0.43 g | 0.070 | 14.00% |
| | 95% X-54 5% Orange Fun | transp. sinks | dissolved, transp. solution | dissolved, transp. solution | dissolved, transp. solution | dissolved, transp. solution | soluble | soluble | 0.500 g | 0 g | 0.500 | 100.00% |
| | 77% X-54 23% Orange Fun | transp. sinks | dissolved, sediment white | dissolved, sediment white | dissolved, sediment white | dissolved, sediment white | soluble | soluble | 0.500 g | 0 g | 0.500 | 100.00% |
| | 95% WF 5% Orange Fun | transp. floats | swells, edges cloudy | swells, edges cloudy | swells, edges cloudy | swells, edges cloudy | sparingly soluble | sparingly soluble | 0.500 g | 0.29 g | 0.210 | 42.00% |
| | 76% WF 24% Orange Fun | transp. floats | swells, edges cloudy | swells, edges cloudy | swells, edges cloudy | swells, edges cloudy | sparingly soluble | soluble | 0.500 g | 0 g | 0.500 | 100.00% |
| | 95% PA 5% Orange Fun | transp. sinks | splits, transp. | splits, transp. | splits, transp. | splits, cloudy | sparingly soluble | soluble | 0.500 g | 0 g | 0.500 | 100.00% |
| | 77% PA 23% Orange Fun | transp. sinks | swells, transp. | swells (more than PA5), transp. | swells (more than PA5), transp. | swells greatly, splits | sparingly soluble | soluble | 0.500 g | 0 g | 0.500 | 100.00% |
| | 95% PE 5% Orange Fun | transp. sinks | partially dissolved, surf. swells, transp. | partially dissolved, surf. swells, transp. | partially dissolved, surf. swells, transp. | more passed into solution | sparingly soluble | soluble | 0.500 g | 0 g | 0.500 | 100.00% |
| | 77% PE 23% Orange Fun | transp. sinks | partially dissolved, surf. swells, center transp. | partially dissolved, surf. swells, center transp. | partially dissolved, surf. swells, center transp. | solution of white sediment | soluble | soluble | 0.500 g | 0 g | 0.500 | 100.00% |
| Polyamide + Marlinat (surfactant) | 86% AF 10% Marlinat 4% Orange Fun | transp. floats | cracks on surf., transp. | cracks on surf., transp. | cracks on surf., transp. | swells readily, cracks, transp. | sparingly soluble | sparingly soluble | 0.500 g | 0.45 g | 0.050 | 10.00% |
| | 65% AF 30% Marlinat 5% Orange Fun | transp. floats | severe cracking, surf. somewhat cloudy | severe cracking, surf. somewhat cloudy | severe cracking, surf. somewhat cloudy | splits greatly, transp. | sparingly soluble | sparingly soluble | 0.500 g | 0.38 g | 0.120 | 24.00% |
| | 86% A 200 10% Marlinat | slightly opaque, floats | swells, center transp. | swells, center transp., | swells, center transp., | no further swelling, cloudy | insoluble | insoluble | 0.500 g | 0.52 g | −0.020 | −4.00% |

TABLE 4-continued

| | | 0 h | 24 h | 48 h | 72 h | 6 days | 8 days | 43 days | Initial weight ca. | Final weight | Difference | Dissolved fraction |
|---|---|---|---|---|---|---|---|---|---|---|---|---|
| | 4% Orange Fun 66% A 200 30% Marlinat 4% Orange Fun | slightly opaque, floats | swells, splits, cloudy | surf. cloudy swells, splits, cloudy | surf. cloudy swells, splits, cloudy | cracks/ breaks matrix, cloudy | insoluble | sparingly soluble | 0.500 g | 0.33 g | 0.170 | 34.00% |
| | 86% PA 10% Marlinat 4% Orange Fun | transp. sinks | surf. cloudy, center transp. | surf. cloudy, center transp. + splits | surf. cloudy, center transp. + splits | splits greatly, cloudy | sparingly soluble | soluble | 0.500 g | 0 g | 0.500 | 100.00% |
| | 66% PA 30% Marlinat 4% Orange Fun | transp. sinks | splits, milky surf. | swells, splits, cloudy | swells, splits, cloudy | swells, splits, milky | sparingly soluble | soluble | 0.500 g | 0 g | 0.500 | 100.00% |
| Polyamide + various water-soluble gel formers | 90% AF 5% Imbentin (11 EO) 5% Orange Fun | transp. floats | splits slightly, cloudy | splits slightly, cloudy | splits slightly, cloudy | splits slightly, cloudy | sparingly soluble | insoluble | 0.500 g | 0.47 g | 0.030 | 6.00% |
| | 66% AF 30% Imbentin (11 EO) 4% Orange Fun | slightly opaque, floats | flakes, splits, cloudy | flakes, splits, cloudy | flakes, splits, cloudy | somewhat dissolved, cracks, cloudy | sparingly soluble | sparingly soluble | 0.500 g | 0.43 g | 0.070 | 14.00% |
| | 83% AF 13% Tego 4% Orange Fun | transp. floats | swells, splits, cloudy | swells, splits, cloudy | swells, splits, cloudy | swollen edges, cloudy | sparingly soluble | sparingly soluble | 0.500 g | 0.45 g | 0.050 | 10.00% |
| | 66.5% AF 30% Tego 3.5% Orange Fun | transp. floats | swells, splits, flakes, cloudy | swells, splits, flakes, cloudy | swells, splits, flakes, cloudy | somewhat dissolved, thick flakes, swells, cloudy | sparingly soluble | sparingly soluble | 0.500 g | 0.29 g | 0.210 | 42.00% |
| | 70% AF 30% Gelatin | transp. floats | swells, splits, flakes, cloudy | swells, splits, flakes, cloudy | swells, splits, flakes, cloudy | splits slightly, flakes, transp. - cloudy | sparingly soluble | sparingly soluble | 0.500 g | 0.4 g | 0.100 | 20.00% |

The table shows the position of the shake experiments after 8 days and after 43 days; after 43 days quantitative evaluation was carried out; for this, the supernatant solutions were extracted by shaking and then the residue was dried for the first 24 h at 40° C. and then left to stand at room temperature for ca. 50 h. The initial weights were ca. 0.5 g (+/−5% weighing error).

The solubility tests were carried out in 30 g of tap water with 0.5 g mass in closeable vessels at room temperature (leaving to stand).

The experiments simulate storage and flushing in the WC, but where flushing is carried out at most only once per day. Flushing means that the supernatant liquid is firstly shaken (simulates the swirling in the cistern) and then decanted off. Fresh tap water is then absorbed again.

AF=Sylvaclear AF 1900
A 200=Sylvaclear A 200
X-54=Sylvaclear X-54-188-152
WF=Sylvaclear WF 1500
PA=Sylvaclear PA 1200
PE=Sylvaclear PE 400 V
Orange Fun=Perfume
Marlinat=Marlinat 242/90T
Imbentin=Imbentin AG/168S/110
Tego=Tego Carbomer 134 Polyacrylate
surf.=Surface

The invention claimed is:

1. A sanitary product in piece form for use in the cistern of a toilet, which sanitary product comprises at least two different gel formers (1, 2) and fragrances, wherein one gel former (gel formers 1) is selected from the group of the polyamide resins and, with hydrophobic liquids, forms water-insoluble or sparingly soluble gels and the fraction of gel formers 1 in the sanitary product is at least 50% by weight, and the other gel former (gel formers 2) is a surfactant, a water-soluble or water-dispersible polyamide resin or a natural or synthetic gel-forming polymer and is water-soluble or water-dispersible and wherein the sanitary product is transparent, gradually flushes away and releases fragrances, and gel formers 1 and 2 are in one phase.

2. The sanitary product as claimed in claim 1, wherein the polyamide resin is selected from the group of the ester-terminated polyamides (ETPA), the ester-terminated, dimeric-acid-based polyamide resins (ETDABP), the amide-terminated polyamides (ATPA) and the polyalkyleneoxy-polyamides (PAOPA).

3. The sanitary product as claimed in claim 1, wherein the surfactant is an anionic, nonionic or amphoteric surfactant.

4. The sanitary product as claimed in claim 1, wherein the fragrance fraction is less than 70% by weight.

5. The sanitary product as claimed in claim 1, wherein the fraction of gel formers 2 in the sanitary product is between 5 and 80% by weight.

6. The sanitary product as claimed in claim 1, wherein the flush numbers of the sanitary product located in a cistern at 16° C. are at least 150.

7. A method for scenting toilets, said method comprising placing into a cistern of a toilet a transparent sanitary product in piece form, the transparent sanitary product comprising at least two different gel formers (1, 2) and fragrances, where one gel former (gel formers 1) is selected from the group of the polyamide resins and forms gels with hydrophobic liquids, which gels are insoluble or sparingly soluble in water, and the fraction of gel formers 1 in the product is at least 50% by weight and the other gel former (gel former 2) is a surfactant, a water-soluble or water-dispersible polyamide resin or a natural or synthetic gel-forming polymer and is water-soluble or water-dispersible, and gel formers 1 and 2 are in one phase, whereupon the transparent sanitary product gradually flushes away and releases fragrances.

8. The sanitary product as claimed in claim 3 wherein the surfactant is selected from the group of the ether sulfates, the sulfonates, and phosphates.

9. The sanitary product as claimed in claim 8 wherein the surfactant is selected from the group of an alkylbenzene-sulfonate, a fatty alcohol polyethylene glycol ether sulfate, an alkyl ether sulfate or an alkyl polyglycol ether phosphate.

10. The sanitary product as claimed in claim 4 wherein the fragrance fraction is between 1 and 40% by weight.

11. The sanitary product as claimed in claim 10 wherein the fragrance fraction is between 3 and 30% by weight.

12. The sanitary product as claimed in claim 11 wherein the fragrance fraction is between 4 and 15% by weight.

13. The sanitary product as claimed in claim 5 wherein the fraction of gel former 2 in the sanitary product is between 8 and 60% by weight.

14. The sanitary product as claimed in claim 13 wherein the fraction of gel formers 2 in the sanitary product is between 15 and 50% by weight.

15. The sanitary product as claimed in claim 6 wherein the flush numbers of the sanitary product located in a cistern at 16° C. are at least 200.

* * * * *